(12) United States Patent
Kim

(10) Patent No.: US 11,793,440 B2
(45) Date of Patent: Oct. 24, 2023

(54) METHOD TO DETECT NOISE IN A WEARABLE CARDIOVERTER DEFIBRILLATOR

(71) Applicant: West Affum Holdings Corp., Grand Cayman (KY)

(72) Inventor: Jaeho Kim, Redmond, WA (US)

(73) Assignee: WEST AFFUM HOLDINGS DAC, Dublin (IE)

(*) Notice: Subject to any disclaimer, the term of this patent is extended or adjusted under 35 U.S.C. 154(b) by 116 days.

(21) Appl. No.: 16/985,803

(22) Filed: Aug. 5, 2020

(65) Prior Publication Data

US 2021/0038107 A1 Feb. 11, 2021

Related U.S. Application Data

(60) Provisional application No. 62/885,122, filed on Aug. 9, 2019.

(51) Int. Cl.
*A61B 5/282* (2021.01)
*A61B 5/00* (2006.01)
*A61N 1/362* (2006.01)
*A61N 1/39* (2006.01)
*A61B 5/316* (2021.01)

(52) U.S. Cl.
CPC .............. *A61B 5/282* (2021.01); *A61B 5/316* (2021.01); *A61B 5/6802* (2013.01); *A61B 5/746* (2013.01); *A61N 1/3625* (2013.01); *A61N 1/3904* (2017.08)

(58) Field of Classification Search
CPC ............................... A61B 5/282; A61N 1/3904
USPC ....................................................... 600/508
See application file for complete search history.

(56) References Cited

U.S. PATENT DOCUMENTS

| 3,724,355 A | 4/1973 | Unger |
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |

(Continued)

FOREIGN PATENT DOCUMENTS

WO 1998039061 A2 9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Nicole F Lavert
(74) *Attorney, Agent, or Firm* — Columbia IP Law

(57) ABSTRACT

In one embodiment, a method to detect noise levels in electrocardiogram (ECG) signals is described. The method includes connecting to at least three sensing electrodes and obtaining a signal from each of the at least three sensing electrodes. The method also includes defining at least three channels between the at least three electrodes. The method includes calculating a morphological similarity value of at least one combination of the at least three channels based at least in part on the obtained signal from each of the at least three sensing electrodes and determining a noise level based at least in part on the calculated morphological similarity value.

20 Claims, 10 Drawing Sheets

(56) References Cited

U.S. PATENT DOCUMENTS

| | | |
|---|---|---|
| 5,228,449 A | 7/1993 | Christ et al. |
| 5,348,008 A | 9/1994 | Born et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 9,724,008 B2 | 8/2017 | Sullivan |
| 9,757,581 B2 | 9/2017 | Sullivan |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2008/0288009 A1* | 11/2008 | Kim ............... A61B 5/287 607/4 |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1* | 11/2012 | Volpe ............... A61N 1/0484 600/512 |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |
| 2018/0116537 A1* | 5/2018 | Sullivan ............... A61N 1/046 |

OTHER PUBLICATIONS

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

* cited by examiner

METHOD TO DETECT NOISE IN A WEARABLE CARDIOVERTER DEFIBRILLATOR

CROSS REFERENCE TO RELATED PATENT APPLICATIONS

This patent application claims benefit of U.S. Provisional Patent Application No. 62/885,122 filed Aug. 9, 2019 and is incorporated herein by reference in their entirety for all purposes.

BACKGROUND

When people suffer from some types of heart arrhythmias, in some instances, blood flow to various parts of the body may be reduced. Some arrhythmias can result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people may include patients who have had a heart attack or a prior SCA episode. A frequent recommendation for these people is to receive an Implantable Cardioverter Defibrillator (ICD). The ICD is surgically implanted in the chest, and continuously monitors the patient's intracardiac electrogram (IEGM). If certain types of heart arrhythmias are detected, then the ICD delivers an electric shock through the heart.

As a further precaution, people who have been identified to have an increased risk of a SCA are sometimes given a Wearable Cardioverter Defibrillator (WCD) system to wear until an ICD is implanted. Early versions of such systems were called wearable cardiac defibrillator systems. A WCD system typically includes a harness, vest, belt, or other garment that the patient wears. The WCD system further includes electronic components, such as a defibrillator and electrodes, coupled to the harness, vest, or another garment. When the patient wears the WCD system, the electrodes may electrically contact the patient's skin, and aid in sensing the patient's electrocardiogram (ECG). If a shockable heart arrhythmia (e.g., ventricular fibrillation or VF) is detected from the ECG, then the defibrillator delivers an appropriate electric shock through the patient's body, and thus through the heart. The delivered shock may restart the patient's heart and save the patient's life.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure describes instances and examples of cardiac monitoring systems (e.g., WCD systems), devices, systems, storage media that may store programs, and methods.

In one embodiment, a method to detect noise levels in electrocardiogram (ECG) signals is described. The method includes connecting to at least three sensing electrodes and obtaining a signal from each of the at least three sensing electrodes. The method also includes defining at least three channels between the at least three electrodes. The method includes calculating a morphological similarity value of at least one combination of the at least three channels based at least in part on the obtained signal from each of the at least three sensing electrodes and determining a noise level based at least in part on the calculated morphological similarity value.

In some embodiments, the method may establish correlating channels based at least in part on the at least three channels. The correlating channels may have a similar morphological similarity value when no noise is present in the ECG signals. An morphological similarity value of each of the correlating channels may be calculated. In some embodiments, the method may include determining if the morphological similarity value of each of the correlating channels meets or exceeds a predetermined threshold. In some embodiments, the predetermined threshold may be equal to or above than 0.2. In some embodiments, the method may include analyzing the obtained signal from each of the at least three sensing electrodes for a shockable heart rhythm when the morphological similarity value is above the predetermined threshold. In some embodiments, the method may include suspending an ECG shockable analysis of the obtained signal from each of the at least three sensing electrodes when the morphological similarity value is below a predetermined analysis threshold.

In further embodiments, the method may include obtaining a second signal from each of the at least three sensing electrodes after a first time period has elapsed and calculating a second morphological similarity value of at least one combination of the at least three channels based at least in part on the second obtained signal from each of the at least three sensing electrodes. In some embodiments, the method may include issuing a noise alert to a person when the when second morphological similarity value is below the predetermined threshold. In some embodiments, calculating the morphological similarity value may include calculating feature coefficient correlation (FCC) values.

In further embodiments, the morphological similarity values are measured using a fixed duration of the obtained signal including and between 3 and 15 seconds. The morphological similarity values may be measured using a fixed duration of 5 seconds.

In another embodiment, a wearable cardioverter defibrillator (WCD) is described. The WCD includes a support structure wearable by a person and a processor coupled to the support structure. The WCD also includes a discharge circuit configured to discharge a stored electrical charge through a body of the patient. The discharge circuit in communication with the processor. The process is configured to connect to at least three sensing electrodes, obtain a signal from each of the at least three sensing electrodes, and define at least three channels between the at least three electrodes. The processor may be configured to calculate a morphological similarity value of at least one combination of the at least three channels based at least in part on the obtained signal from each of the at least three sensing electrodes and determine a noise level based at least in part on the calculated morphological similarity value.

In some embodiments, the processor may be further configured to establish correlating channels based at least in part on the at least three channels, wherein the correlating channels have a similar morphological similarity value when no noise is present in the ECG signals and calculate an morphological similarity value of each of the correlating channels. In some embodiments, the processor may be further configured to determine when the morphological similarity value of each of the correlating channels meets or exceeds a predetermined threshold. In some embodiments, the predetermined threshold may be equal to or above 0.2.

In further embodiments, the processor may be further configured to analyze the obtained signal from each of the at least three sensing electrodes for a shockable heart rhythm when the morphological similarity value is below a predetermined analysis threshold. In some embodiments, the predetermined analysis threshold may be below 0.2. In some embodiments, the processor may be further configured to suspend ECG shockable analysis of the obtained signal from each of the at least three sensing electrodes when the morphological similarity value is does not satisfy the predetermined threshold. In some embodiments, the processor may be further configured to obtain a second signal from each of the at least three sensing electrodes after a first time period has elapsed and calculate a second morphological similarity value of at least one combination of the at least three channels based at least in part on the second obtained signal from each of the at least three sensing electrodes.

In further embodiments, the processor may be configured to issue a noise alert to a person when the when second morphological similarity value does not meet or exceed the predetermined threshold. In some embodiments, calculating the morphological similarity values may include calculating feature correlation coefficient (FCC) values. In some embodiments, the morphological similarity values may be measured using a fixed duration including and between 3 and 15 seconds. In some embodiments, the morphological similarity values may be measured using a fixed duration of 5 seconds.

In another embodiment, a method to detect noise levels in electrocardiogram (ECG) signals is described. The method includes positioning at least four ECG sensing electrodes to measure electrical activity of a heart of a person and receiving at least three ECG signals from at least three of the at least four ECG electrodes. The method also includes defining at least three channels between the at least three electrodes, calculating a morphological similarity value of at least one combination of the at least three channels based at least in part on the obtained signal from each of the at least three sensing electrodes, and determining a noise level based at least in part on the calculated morphological similarity value.

BRIEF DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCDs) are worn by patients at risk for sudden cardiac arrest. When a patient wears a WCD, the WCD may need to alert the patient throughout its use, and in some instances, may need to shock the patient. However, in some instances, the WCD may inaccurately calculate the patient's heart rate which may result in a frequent rhythm analysis or cause an inappropriate shock treatment. As discussed herein, a cross correlation-based noise measurement method may improve the accuracy of noise detection which may avoid inaccurate Heart Rate calculations. This may lead to reduced false shock alert which can cause patient stress and inappropriate shock treatments.

For example, some WCD systems may be unable to discriminate between noise that may interfere with a rhythm analysis and noise that the rhythm analysis will tolerate. An ideal noise detection algorithm will only trigger a patient for noise that interferes with the rhythm analysis. This avoids undue stress on the patient for incessant or unnecessary alarms. When a noise is present, a noise alert should be issued rather than a shock alert. Shock alerts are much more urgent and may overly stress the patient.

For example, a WCD may have multiple ECG vectors from multiple electrodes for monitoring the patient. At any given point in time, some of these vectors may produce a relatively cleaner ECG signal and some may produce a noisier signal. Since the detected heart rate is typically used to detect the onset of the ventricular tachyarrhythmia or to classify the rhythms, the inaccurate heart rate calculation can request a frequent rhythm analysis or cause an inappropriate shock treatment.

Figure 1:
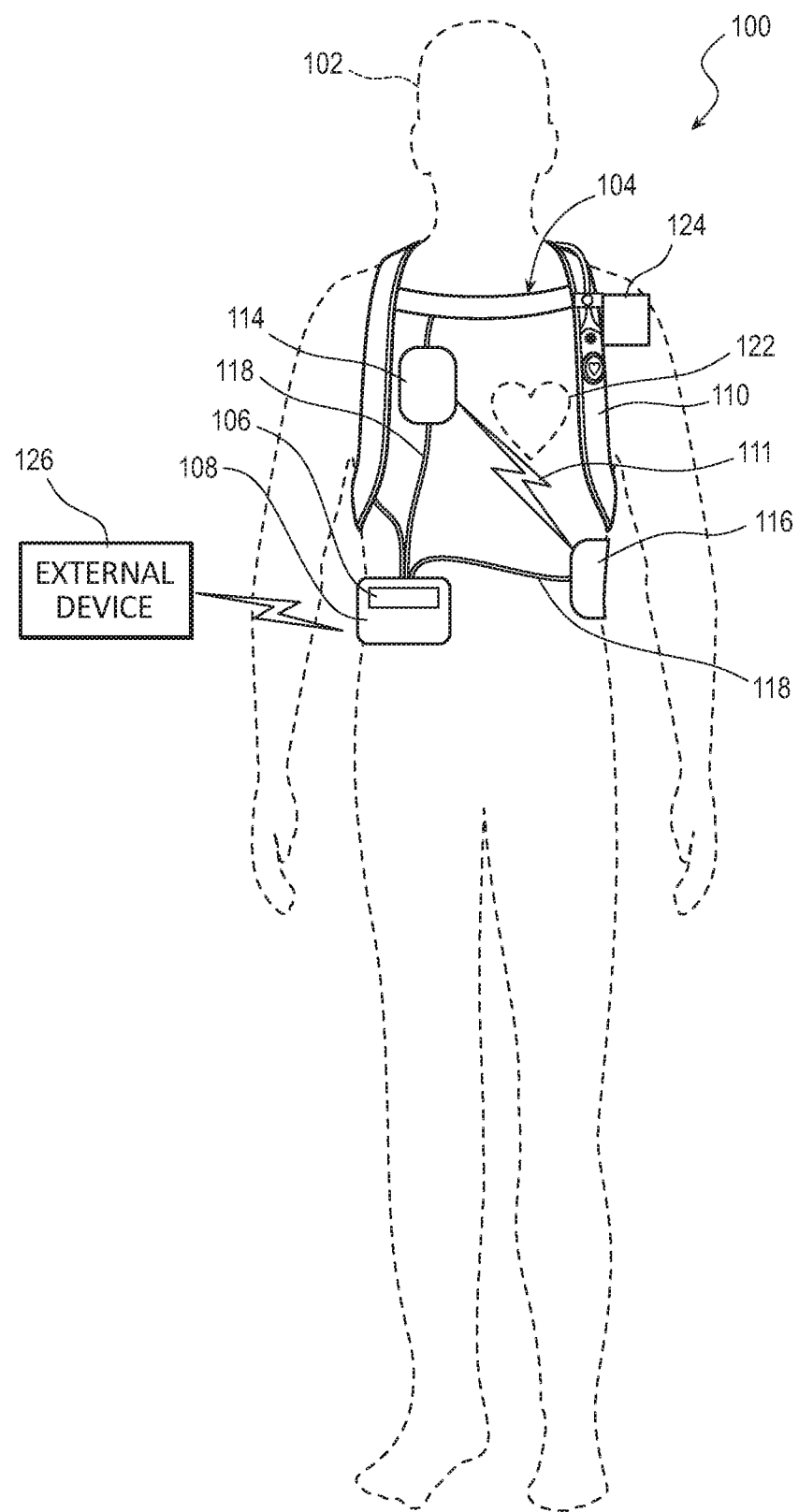
FIG. 1 is a diagram of a sample WCD system in accordance with exemplary embodiments described herein.

FIG. 1 illustrates a system 100 with a patient 102 wearing an example of a WCD system 104 according to embodiments described herein. In some embodiments, the WCD system 104 may include one or more communication devices 106, a support structure 110, and an external defibrillator 108 connected to two or more defibrillation electrodes 114, 116, among other components.

The support structure 110 may be worn by the patient 102. The patient 102 may be ambulatory, meaning the patient 102 can walk around and is not necessarily bed-ridden while wearing the wearable portion of the WCD system 104. While the patient 102 may be considered a "user" of the WCD system 104, this is not a requirement. For instance, a user of the WCD system 104 may also be a clinician such as a doctor, nurse, emergency medical technician (EMT) or other similarly tasked individual or group of individuals. In some cases, a user may even be a bystander. The particular context of these and other related terms within this description should be interpreted accordingly.

In some embodiments, the support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component of the support structure 110 may additionally carry or couple to all of the various components of the WCD system 104.

In other embodiments, the support structure 110 may comprise multiple components. For example, the support structure 110 may include a first component resting on a patient's shoulders. The first component may properly locate a series of defibrillation electrodes 114, 116 on the torso 112 of the patient 102. A second component may rest more towards a patient's hips, whereby the second component may be positioned such that the patient's hips support the heavier components of the WCD system 104. In some embodiments, the heavier components of the WCD system 104 may be carried via a shoulder strap or may be kept close to the patient 102 such as in a cart, bag, stroller, wheelchair, or other vehicle.

The external defibrillator 108 may be coupled to the support structure 110 or may be carried remotely from the patient 102. The external defibrillator 108 may be triggered to deliver an electric shock to the patient 102 when patient 102 wears the WCD system 104. For example, if certain thresholds are exceeded or met, the external defibrillator 108 may engage and deliver a shock to the patient 102.

The defibrillation electrodes 114, 116 can be configured to be worn by patient 102 in a number of ways. For instance, the defibrillator 108 and the defibrillation electrodes 114, 116 can be coupled to the support structure 110 directly or indirectly. For example, the support structure 110 can be configured to be worn by the patient 102 to maintain at least one of the electrodes 114, 116 on the body of the patient 102, while the patient 102 is moving around, etc. The electrodes 114, 116 can be thus maintained on the torso 112 by being attached to the skin of patient 102, simply pressed against the skin directly or through garments, etc. In some embodiments, the electrodes 114, 116 are not necessarily pressed against the skin but becomes biased that way upon sensing a condition that could merit intervention by the WCD system 104. In addition, many of the components of defibrillator 108 can be considered coupled to support structure 110 directly, or indirectly via at least one of defibrillation electrodes 114, 116.

The WCD system 104 may defibrillate the patient 102 by delivering an electrical charge, pulse, or shock 111 to the patient 102 through a series of electrodes 114, 116 positioned on the torso 112. For example, when defibrillation electrodes 114, 116 are in good electrical contact with the torso 112 of patient 102, the defibrillator 108 can administer, via electrodes 114, 116, a brief, strong electric pulse 111 through the body. The pulse 111 is also known as shock, defibrillation shock, therapy, electrotherapy, therapy shock, etc. The pulse 111 is intended to go through and restart heart 122, in an effort to save the life of patient 102. The pulse 111 can further include one or more pacing pulses of lesser magnitude to pace heart 122 if needed. The electrodes 114, 116 may be electrically coupled to the external defibrillator 108 via a series of electrode leads 118. The defibrillator 108 may administer an electric shock 111 to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116.

In some embodiments, the WCD system 104 may also include either an external or internal monitoring device or some combination thereof. FIG. 1 displays an external monitoring device 124 which may also be known as an outside monitoring device. The monitoring device 124 may monitor at least one local parameter. Local parameters may include a physical state of the patient 102 such as ECG, movement, heartrate, pulse, temperature, and the like. Local parameters may also include a parameter of the WCD 104, environmental parameters, or the like. The monitoring device 124 may be physically coupled to the support structure 110 or may be proximate the support structure 110. In either location, the monitoring device 124 is communicatively coupled with other components of the WCD 104.

For some of these parameters, the device 124 may include one or more sensors or transducers. Each one of such sensors can be configured to sense a parameter of the patient 102, and to render an input responsive to the sensed parameter. In some embodiments, the input is quantitative, such as values of a sensed parameter; in other embodiments, the input is qualitative, such as informing whether or not a threshold is crossed. In some instances, these inputs about the patient 102 are also referred to herein as patient physiological inputs and patient inputs. In some embodiments, a sensor can be construed more broadly, as encompassing many individual sensors.

In some embodiments, a communication device 106 may enable the patient 102 to interact with, and garnish data from, the WCD system 104. The communication device 106 may enable a patient or third party to view patient data, dismiss a shock if the patient is still conscious, turn off an alarm, and otherwise engage with the WCD system 104. In some embodiments, the communication device 106 may be a separable part of an external defibrillator 108. For example, the communication device 106 may be a separate device coupled to the external defibrillator 108. In some embodiments, the communication device 106 may be wired or wirelessly linked to the external defibrillator 108 and may be removable from the defibrillator 108. In other embodiments, the communication device 106 may form an inseparable assembly and share internal components with the external defibrillator 108. In some embodiments, the WCD system 104 may include more than one communication device 106. For example, the defibrillator 108 may include components able to communicate to the patient and the WCD system 104 may include a separate communication device 106 remote form the defibrillator 108.

In some embodiments, the defibrillator 108 may connect with one or more external devices 126. For example, as shown in FIG. 1, the defibrillator 108 may connect to various external devices 126 such as a the cloud, a remote desktop, a laptop, a mobile device, or other external device using a network such as the Internet, local area networks, wide area networks, virtual private networks (VPN), other communication networks or channels, or any combination thereof.

In embodiments, one or more of the components of the exemplary WCD system 104 may be customized for the patient 102. Customization may include a number of aspects including, but not limited to, fitting the support structure 110 to the torso 112 of patient 102; baseline physiological parameters of patient 102 can be measured, such as the heart rate of patient 102 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and the like. Moreover, a programming interface can be made according to embodiments, which receives such measured values of baseline physiological parameters. Such a programming interface may input automatically in the WCD system these, along with other data.

Figure 2:
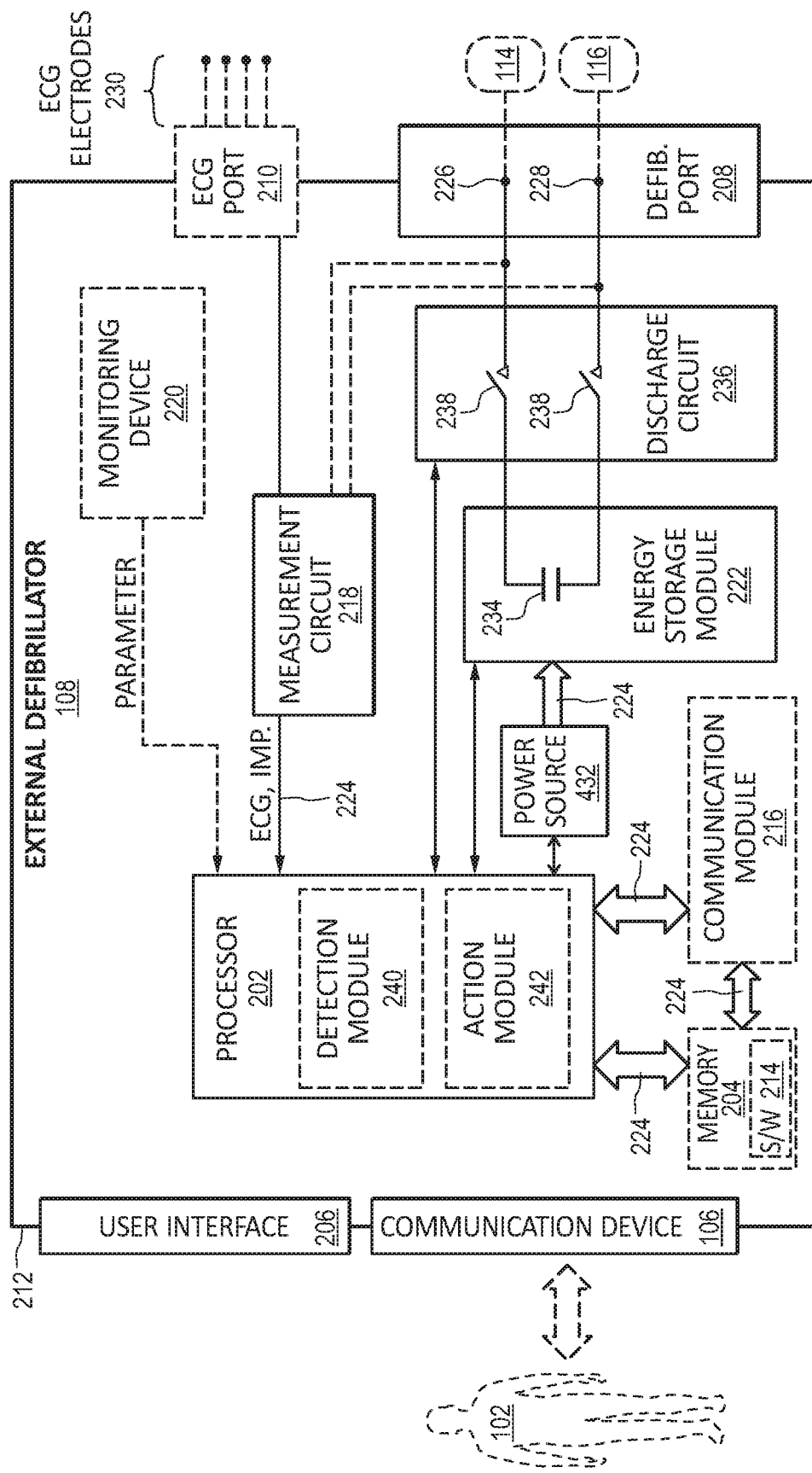
FIG. 2 is a block diagram of an example defibrillator in accordance with exemplary embodiments described herein.

FIG. 2 is a diagram displaying various components of an example external defibrillator 108. The external defibrillator 108 may be an example of the defibrillator 108 described with reference to FIG. 1. The components shown in FIG. 2 may be contained within a single unit or may be separated amongst two or more units in communication with each other. The defibrillator 108 may include a communication device 106, processor 202, memory 204, defibrillation port 208, and ECG port 210, among other components. In some embodiments, the components are contained within a housing 212 or casing. The housing 212 may comprise a hard shell around the components or may comprise a softer shell for increased patient comfort.

The communication device 106, processor 202, memory 204 (including software/firmware code (SW) 214), defibrillation port 208, ECG port 210, communication module 216, measurement circuit 218, monitoring device 220, and energy storage module 222 may communicate, directly or indirectly, with one another via one or more buses 224. The one or more buses 224 may allow data communication between the elements and/or modules of the defibrillator 108.

The memory 204 may include random access memory (RAM), read only memory (ROM), flash RAM, and/or other types. The memory 204 may store computer-readable, computer-executable software/firmware code 214 including instructions that, when executed, cause the processor 202 to perform various functions (e.g., determine shock criteria, determine consciousness of patient, track patient parameters, establish electrode channels, determine noise levels in electrode readings, etc.). In some embodiments, the processor 202 may include an intelligent hardware device, e.g., a central processing unit (CPU), a microcontroller, an application-specific integrated circuit (ASIC), etc.

In some embodiments, the memory 204 can contain, among other things, the Basic Input-Output system (BIOS) which may control basic hardware and/or software operations such interactions and workings of the various components of the defibrillator 108, and in some embodiments, components external to the defibrillator 108. For example, the memory 204 may contain various modules to implement the workings of the defibrillator 108 and other aspects of the present disclosure.

In some embodiments, the defibrillator 108 may include a user interface 206. The user interface 406 may be in addition to or part of the communication device 106. The user interface 406 may display an ECG of the patient, a status of the defibrillator 108, a status of a charge (e.g. a battery charge or an energy storage module), and the like.

In some embodiments, the defibrillator 108 may include a defibrillation port 208. The defibrillation port 208 may comprise a socket, opening, or electrical connection in the housing 212. In some instances, the defibrillation port 208 may include two or more nodes 226, 228. The two or more nodes 226, 228 may accept two or more defibrillation electrodes (e.g. defibrillation electrodes 114, 116, FIG. 1). The nodes 226, 228 may provide an electrical connection between the defibrillation electrodes 114, 116 and the defibrillator 108. The defibrillation electrodes 114, 116 may plug into the two or more nodes 226, 228 via one or more leads (e.g. leads 118), or, in some instances, the defibrillation electrodes 114, 116 may be hardwired to the nodes 226, 228. Once an electrical connection is established between the defibrillation port 208 and the electrodes 114, 116, the defibrillator 108 may be able to deliver an electric shock to the patient 102.

In some embodiments, the defibrillator 108 may include an ECG port 210 in the housing 212. The ECG port 210 may accept one or more ECG electrodes 230 or ECG leads. In some instances, the ECG electrodes 230 sense a patient's ECG signal. For example, the ECG electrodes 230 may record electrical activity generated by heart muscle depolarization. The ECG electrodes 230 may utilize 4-leads to 12-leads or multichannel ECG, or the like. The ECG electrodes 230 may connect with the patient's skin.

In some embodiments, the defibrillator 108 may include a measurement circuit 218. The measurement circuit 218 may be in communication with the ECG port 210. For example, the measurement circuit 218 may receive physiological signals from ECG port 210. The measurement circuit 218 may additionally or alternatively receive physiological signals via the defibrillation port 208 when defibrillation electrodes 114, 116 are attached to the patient 102. The measurement circuit 218 may determine a patient's ECG signal from a difference in voltage between the defibrillation electrodes 114, 116.

In some embodiments, the measurement circuit 218 may monitor the electrical connection between the defibrillation electrodes 114, 116 and the skin of the patient 102. For example, the measurement circuit 218 can detect impedance between electrodes 114, 116. The impedance may indicate the effective resistance of an electric circuit. An impedance calculation may determine when the electrodes 114, 116 have a good electrical connection with the patient's body.

In some embodiments, the defibrillator 108 may include an internal monitoring device 220 within the housing 212. The monitoring device 220 may monitor at least one local parameter. Local parameters may include physical state of the patient such as ECG, movement, heartrate, pulse, temperature, and the like. Local parameters may also include a parameter of the WCD system (e.g. WCD 104, FIG. 1), defibrillator 108, environmental parameters, or the like.

In some embodiments, the WCD system 104 may include an internal monitoring device 220 and an external monitoring device (e.g. external monitoring device 124). If both monitoring devices 124, 220 are present, the monitoring devices 124, 220 may work together to parse out specific parameters depending on position, location, and other factors. For example, the external monitoring device 124 may monitor environmental parameters while the internal monitoring device 220 may monitor patient and system parameters.

In some embodiments, the defibrillator 108 may include a power source 232. The power source 232 may comprise a battery or battery pack, which may be rechargeable. In some instances, the power source 232 may comprise a series of different batteries to ensure the defibrillator 108 has power. For example, the power source 232 may include a series of rechargeable batteries as a prime power source and a series of non-rechargeable batteries as a secondary source. If the patient 102 is proximate an AC power source, such as when sitting down, sleeping, or the like, the power source 232 may include an AC override wherein the power source 232 draws power from the AC source.

In some embodiments, the defibrillator 108 may include an energy storage module 222. The energy storage module 222 may store electrical energy in preparation or anticipation of providing a sudden discharge of electrical energy to the patient. In some embodiments, the energy storage module 222 may have its own power source and/or battery pack. In other embodiments, the energy storage module 222 may pull power from the power source 232. In still further embodiments, the energy storage module 222 may include one or more capacitors 234. The one or more capacitors 234 may store an electrical charge, which may be administered to the patient. The processor 202 may be communicatively coupled to the energy storage module 222 to trigger the amount and timing of electrical energy to provide to the defibrillation port 208 and, subsequently, the patient 102.

In some embodiments, the defibrillator 108 may include a discharge circuit 236. The discharge circuit 236 may control the energy stored in the energy storage module 222. For example, the discharge circuit 236 may either electrical couple or decouple the energy storage module 222 to the defibrillation port 208. The discharge circuit 236 may be communicatively coupled to the processor 202 to control when the energy storage module 222 and the defibrillation port 208 should or should not be coupled to either administer or prevent a charge from emitting from the defibrillator 108. In some embodiments, the discharge circuit 236 may include on or more switches 238. In further embodiments, the one or more switches 238 may include an H-bridge.

In some embodiments, the defibrillator 108 may include a communication module 216. The communication module 216 may establish one or more communication links with either local hardware and/or software to the WCD system 104 and defibrillator 108 or to remote hardwire separate from the WCD system 104. In some embodiments, the communication module 216 may include one or more antennas, processors, and the like. The communication module 216 may communicate wirelessly via radio frequency, electromagnetics, local area networks (LAN), wide area networks (WAN), virtual private networks (VPN), RFID, Bluetooth, cellular networks, and the like. The communication module 216 may facilitate communication of data and commands such as patient data, episode information, therapy attempted, CPR performance, system data, environmental data, and so on.

In some embodiments, the processor 202 may execute one or more modules. For example, the processor 202 may execute a detection module 240 and/or an action module 242. The detection module 240 may be a logic device or algorithm to determine if any or a variety of thresholds are exceeded which may require action of the defibrillator 108. For example, the detection module 240 may receive and interpret all of the signals from the ECG port 210, the defibrillation port 208, the monitoring device 220, an external monitoring device, and the like. The detection module 240 may process the information to ensure the patient is still conscious and healthy. If any parameter indicates the patient 102 may be experiencing distress or indicating a cardiac episode, the detection module 240 may activate the action module 242.

The action module 242 may receive data from the detection module 240 and perform a series of actions. For example, an episode may merely be a loss of batter power at the power source 232 or the energy storage module 222, or one or more electrodes (e.g., ECG electrodes, defibrillation electrodes) may have lost connection. In such instances, the action module 242 may trigger an alert to the patient or to an outside source of the present situation. This may include activating an alert module. If an episode is a health risk, such as a cardiac event, the action module 242 may begin a series of steps. This may include issuing a warning to the patient, issuing a warning to a third party, priming the energy storage module 222 for defibrillation, releasing one or more conductive fluids proximate defibrillation electrodes 114, 116, and the like.

Figure 3:
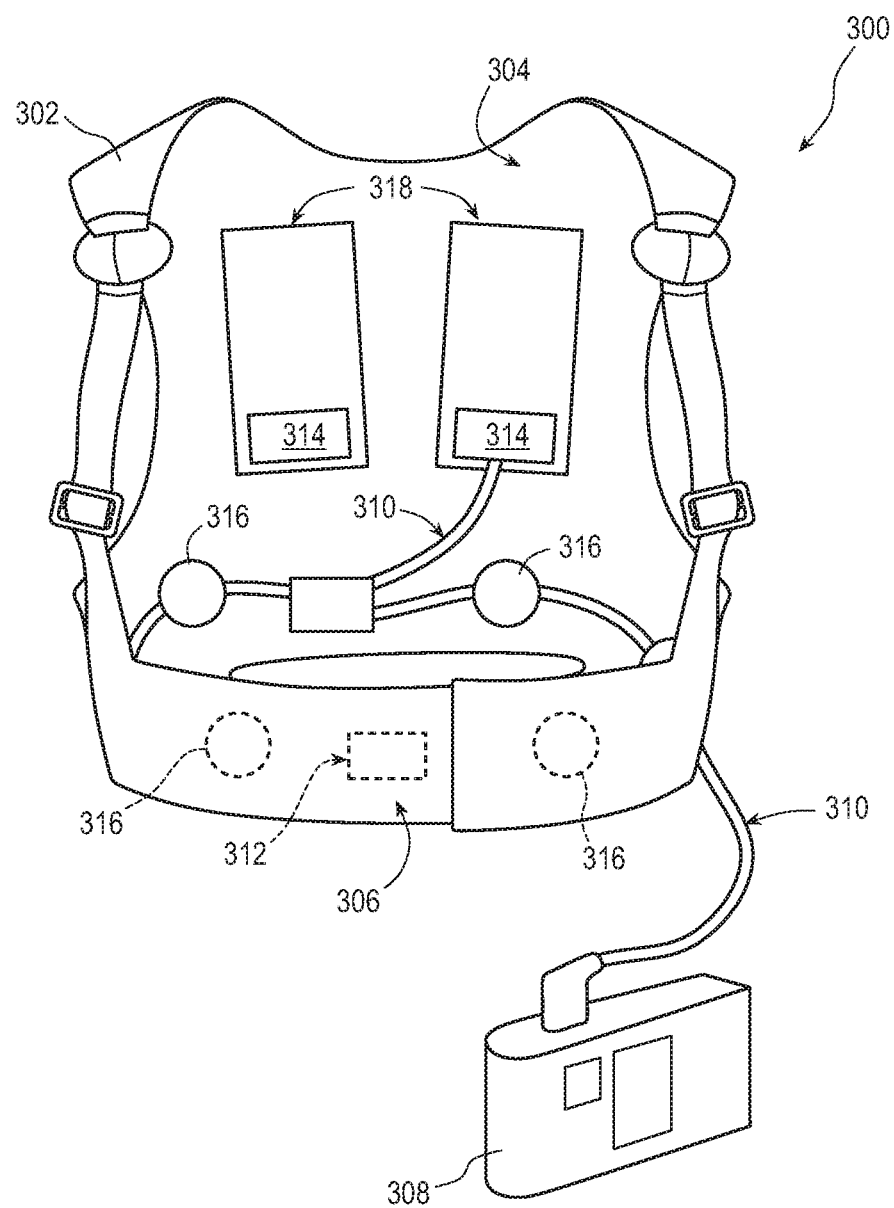
FIG. 3 is a diagram of sample embodiments of components of a WCD system in accordance with exemplary embodiments described herein.

FIG. 3 is a diagram of sample embodiments of components of a WCD system 300 according to exemplary embodiments. The WCD system 300 may be an example of the WCD system 104 describe with reference to FIG. 1. In some embodiments, the WCD system 300 may include a support structure 302 comprising a vest-like wearable garment. In some embodiments, the support structure 302 has a back side 304, and a front side 306 that closes in front of the chest of the patient.

In some embodiments, the WCD system 300 may also include an external defibrillator 308. The external defibrillator 308 may be an example of the defibrillator 108 describe with reference to FIGS. 1 and 2. As illustrated, FIG. 3 does not show any support for the external defibrillator 308, but as discussed, the defibrillator 308 may be carried in a purse, on a belt, by a strap over the shoulder, and the like as discussed previously. One or more wires 310 may connect the external defibrillator 308 to one or more electrodes 312, 314, 316. Of the connected electrodes, electrodes 312, 314 are defibrillation electrodes, and electrodes 316 are ECG sensing electrodes.

The support structure 302 is worn by the patient to maintain electrodes 312, 314, 316 on a body of the patient. For example, the back-defibrillation electrodes 314 are maintained in pockets 318. In some embodiments, the inside of pockets 318 may comprise loose netting, so that the electrodes 314 can contact the back of the patient. In some instances, a conductive fluid may be deployed to increase connectivity. Additionally, in some embodiments, sensing electrodes 316 are maintained in positions that surround the patient's torso, for sensing ECG signals and/or the impedance of the patient.

In some instances, the ECG signals in a WCD system 300 may comprise too much electrical noise to be useful. To ameliorate the problem, multiple ECG sensing electrodes 316 are provided, for presenting many options to the processor (202. The multiple ECG sensing electrodes 316 provide different vectors for sensing the ECG signal of the patient.

Figure 4:
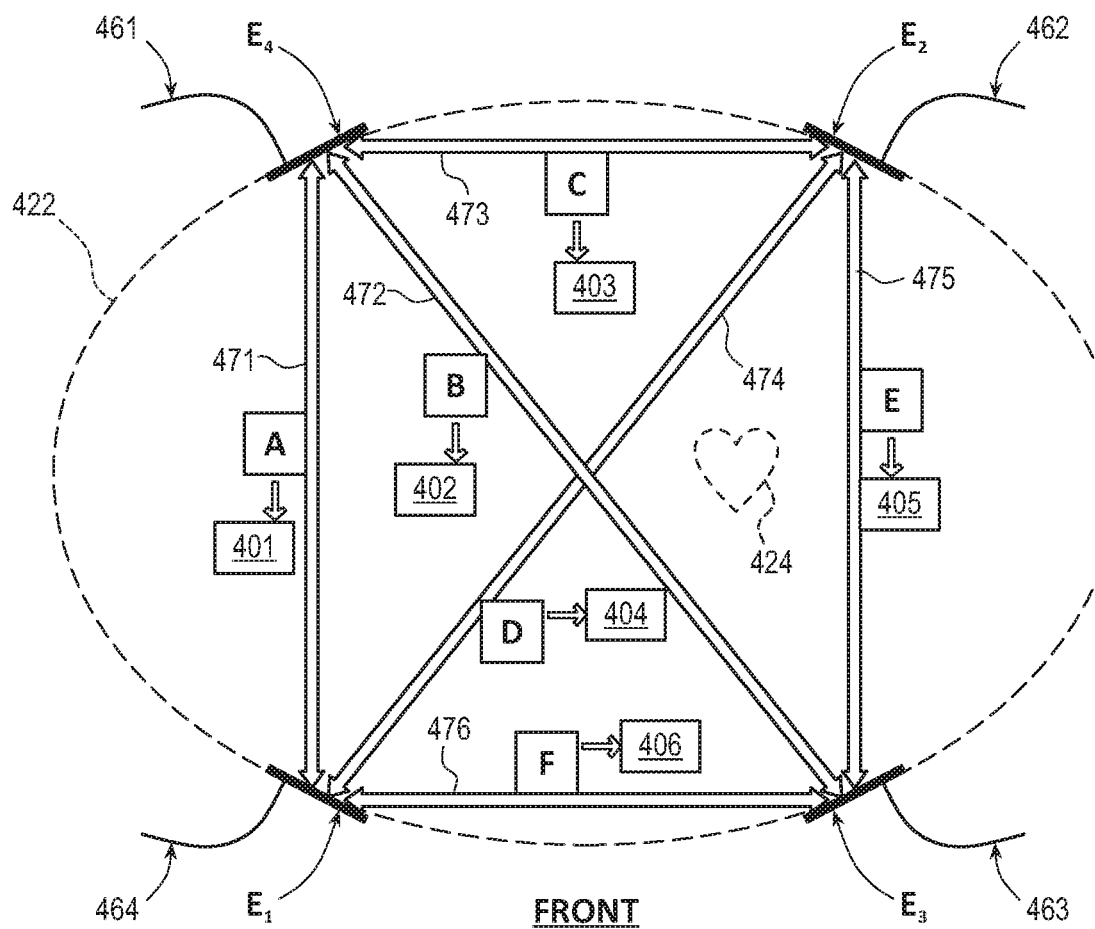
FIG. 4 is a conceptual diagram illustrating multiple electrodes of a WCD system in accordance with exemplary embodiments described herein.

FIG. 4 is a conceptual diagram illustrating how multiple electrodes of a WCD system may defined a multi-vector embodiment for sensing ECG signals along different vectors according to various exemplary embodiments. A crosssection of a body of a patient 422 having a heart 424 is illustrated. In FIG. 4, the patient 422 is viewed from the top looking down and the plane of FIG. 4 intersects patient 422 proximate the torso of the patient 422.

In some embodiments, four ECG sensing electrodes $E_1$, $E_2$, $E_3$, $E_4$ are maintained on the torso of patient 482, and have respective wire leads 461, 462, 463, 464. The electrodes $E_1$, $E_2$, $E_3$, $E_4$ that surround the torso may be similar to the sensing electrodes 316 as described with reference to FIG. 3.

Any pair of these four ECG sensing electrodes $E_1$, $E_2$, $E_3$, $E_4$ defines a vector, along which an ECG signal may be sensed and, in some instances, measured. As such, electrodes $E_1$, $E_2$, $E_3$, $E_4$ define six vectors 471, 472, 473, 474, 475, 476.

These vectors 471, 472, 473, 474, 475, 476 define channels A, B, C, D, E, F respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

As shown FIG. 4, electrodes $E_1$, $E_2$, $E_3$, $E_4$ are drawn on the same plane for simplicity, while in actuality the electrodes $E_1$, $E_2$, $E_3$, $E_4$ may not be positioned on the same plane. Accordingly, vectors 471, 472, 473, 474, 475, 476 are not necessarily on the same plane, either. Further, in some embodiments, the WCD system averages a value of the voltages of all four electrodes electronically and then determines the voltage of each electrode relative to the average value. Conceptually, this average value is the signal at some point in space in between the electrodes $E_1$, $E_2$, $E_3$, $E_4$. It continuously changes its virtual position based on the voltages of the electrodes $E_1$, $E_2$, $E_3$, $E_4$. In some embodiments, this virtual point is referred to herein as the M Central Terminal (MCT). Relative to the MCT, there are four resulting vectors: E1C=E1−CM, E2C=E2−CM, E3C=E3−CM and E4C=E4−CM, where CM is the average voltage value. In some embodiments, the vectors are virtually formed by selecting a pair of these signals and subtracting one from the other. For example, E1C−E2C=(E1−CM)−(E2−CM)=E1−E2+(CM−CM)=E1−E2=E12. Although six vectors are described in FIG. 4, a different number of vectors may be used depending on the number of ECG electrodes present in the system and the desired number of vectors (up to the number of vectors that can be derived from the number of electrodes).

In some embodiments, to make the shock/no-shock determination as accurate as possible, a WCD system may assess the best ECG signals 401, 402, 403, 404, 405, 406 for rhythm analysis and interpretation. For example, ECG signals with the most noise may be ignored, discarded, or not considered, leaving the remaining ECG signals as candidates for the shock/no shock determination.

In other embodiments, the vectors may be aggregated to make a shock/no shock decision, and/or to determine the patient's heart rate and/or QRS widths. For example, in some embodiments the aggregation can be implemented as disclosed in U.S. Pat. No. 9,757,581 issued Sep. 12, 2017 entitled "WEARABLE CARDIOVERTER DEFIBRILLATOR COMPONENTS MAKING AGGREGATE SHOCK/NO SHOCK DETERMINATION FROM TWO OR MORE ECG SIGNALS," which is incorporated herein by reference.

Figure 5:
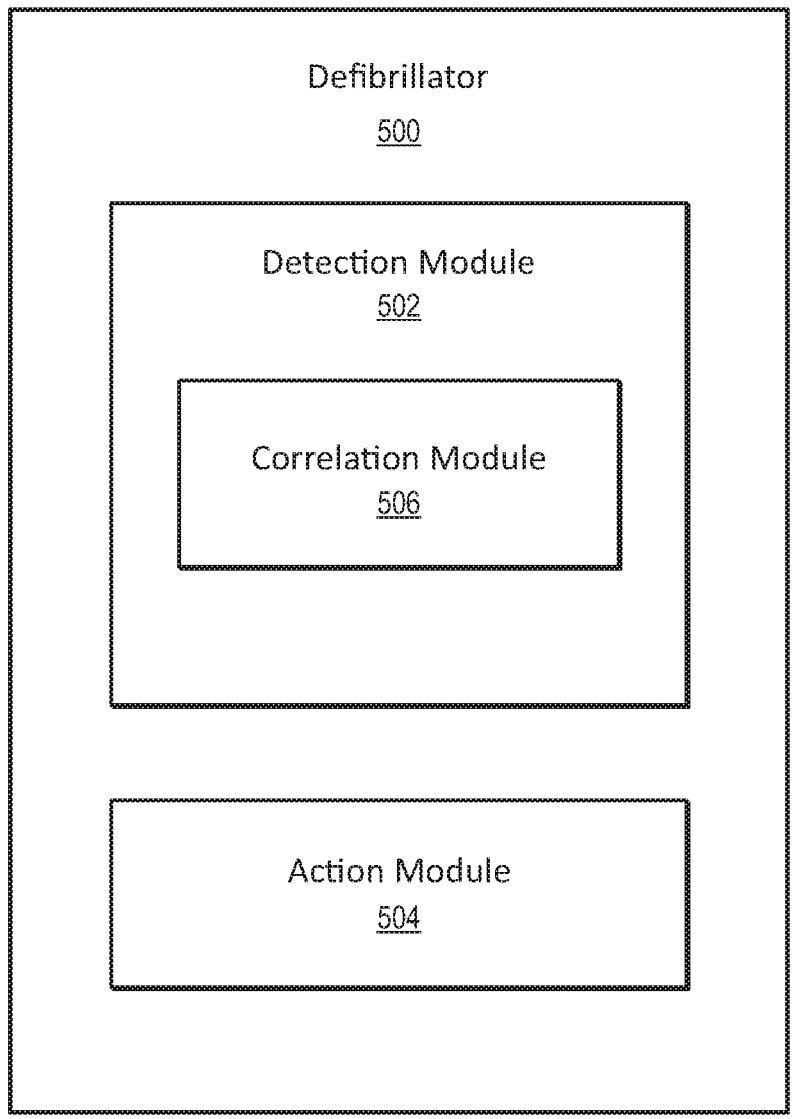
FIG. 5 is a is a block diagram of an example defibrillator in accordance with exemplary embodiments described herein.

FIG. 5 is a block diagram illustrating components of one example of a defibrillator 500. The defibrillator 500 may be an example of the defibrillator 108 described with reference to FIGS. 1 and 2 and defibrillator 308 described with reference to FIG. 3. In this example, the defibrillator 500 has detection module 502 and an alert module 504. The detection module 502 may further include a correlation module 506.

The correlation module 506 may determine the correlation between the available electrode channels (e.g. channels A, B, C, D, E, F described with reference to FIG. 4). As mentioned previously, all electrode channels may not be available. One or more electrodes may be "off" thereby nullifying any correlation or analysis on an electrode channel in relation to the "off" electrode. An electrode may be considered "off" if a reading from the electrode is unavailable. This may be caused by poor contact with the patient's skin, poor connectivity with the defibrillator, a faulty wire, or the like.

For example, if two or more electrodes are off, the correlation module 506 may suspend the analysis, and no decision is made because two channels are used to generate a correlation. However, when only one electrode is off, then at least two differential vectors are available for a rhythm analysis. For example, if electrode $E_3$ is off then the correlation module 415 can analyze channel C and D for correlation and rhythm analysis. In this example, the potential difference between electrode $E_1$ and electrode $E_4$ is small and the morphologies of channels C and D are similar, and the morphologies of channels B and channel F are similar. The correlation module 506 can measure this similarity using a cross-correlation. In some embodiments, the correlation module 506 may calculate a feature correlation coefficient (FCC) of the channels to determine the similarity of the correlations which may determine a noise level of the electrode readings and the potential accuracy of a rhythm analysis.

In some embodiments, ECG signal morphology is the morphology or shape of the QRS complex waveforms. The FCC value measures how similar QRS complexes are between various available channels. The FCC value ranges from 0 (no correlation) to 1 (complete correlation). Therefore, a value close to 1 indicates the QRS waveforms are correlated, or very similar. For example, normalized area difference calculates the area difference after the amplitudes are normalized. The total area difference is compared to the total signal area. This cross-correlation is amplitude independent. For example, two channels may have similar morphology but at different peak amplitudes. In another embodiment, the analysis may focus on frequency domain.

In some embodiments, the correlation module 506 may calculate the FCC as the squared feature correlation coefficient when analyzing a reference vector and a high rate beat vector. The FCC values are calculated for normal sinus rhythm and VF using data between the various channels or vectors. Due to sensor location, channels based on sensors that are close together are expected to be similar in morphology and have a high FCC value. Correspondingly, sensors that are further apart are not as similar in morphology and do not have as high of an FCC value. One example of an FFC calculation with a template with eight feature point is:

$$FCC = \frac{\left(8\sum_{i=1}^{8} x_i y_i - \left(\sum_{i=1}^{8} x_i\right)\left(\sum_{i=1}^{8} y_i\right)\right)^2}{\left(8\sum_{i=1}^{8} x_i^2 - \left(\sum_{i=1}^{8} x_i\right)^2\right)\left(8\sum_{i=1}^{8} y_i^2 - \left(\sum_{i=1}^{8} y_i\right)^2\right)}$$

In one example, during a normal rhythm, exemplary FCC values between the differential vectors are shown below. The comparison of the different vectors displays the correlation of the normal sinus rhythm (NSR) which is a rhythm that originates from a sinus node and describes a characteristic rhythm of a healthy heart. The ventricular fibrillation is an abnormal heart rhythm in which the ventricles of the heart quiver instead of pumping normally. The FCC calculation can be performed for either NSR or VF to reveal noise in the system.

TABLE 1

FCC Values between Exemplary Vectors for Example ECGs

| | Ch D-Ch C | ChD-ChB | Ch F-Ch C | Ch F-Ch D |
|---|---|---|---|---|
| NSR | 0.98 | 0.94 | 0.89 | 0.91 |
| VF | 0.94 | 0.42 | 0.21 | 0.92 |

In the example given, the correlation between channel D-channel C and channel F-channel D is very strong. A strong correlation will be very close to 1. Also, as shown above, the correlation between channel D-channel B and channel F-channel C is weak. A weak correlation may be an FCC value of 0.2 or lower.

In some embodiments, when one electrode $E_3$ is off, channel D and channel C should show a strong correlation. If either $E_1$ or $E_4$ is off, the remaining available channels should show weak but some correlation. The correlation of channels relates to the location of the available electrodes. Channels with similar propagation vectors of the heart should have relatively high FCC values when cross-correlated to each other. In contrast, channels with differing propagation vectors of the heart do not show as high of an FCC correlation. If the correlation is too low as described above, then the situation is considered noisy and the correlation module 506 may suspend rhythm analysis for a predetermined time period. The predetermined time period may be a short duration such 5 seconds or 30 seconds. In some embodiments, the duration may be longer, such as 1 minute or 5 minutes.

Figure 6:
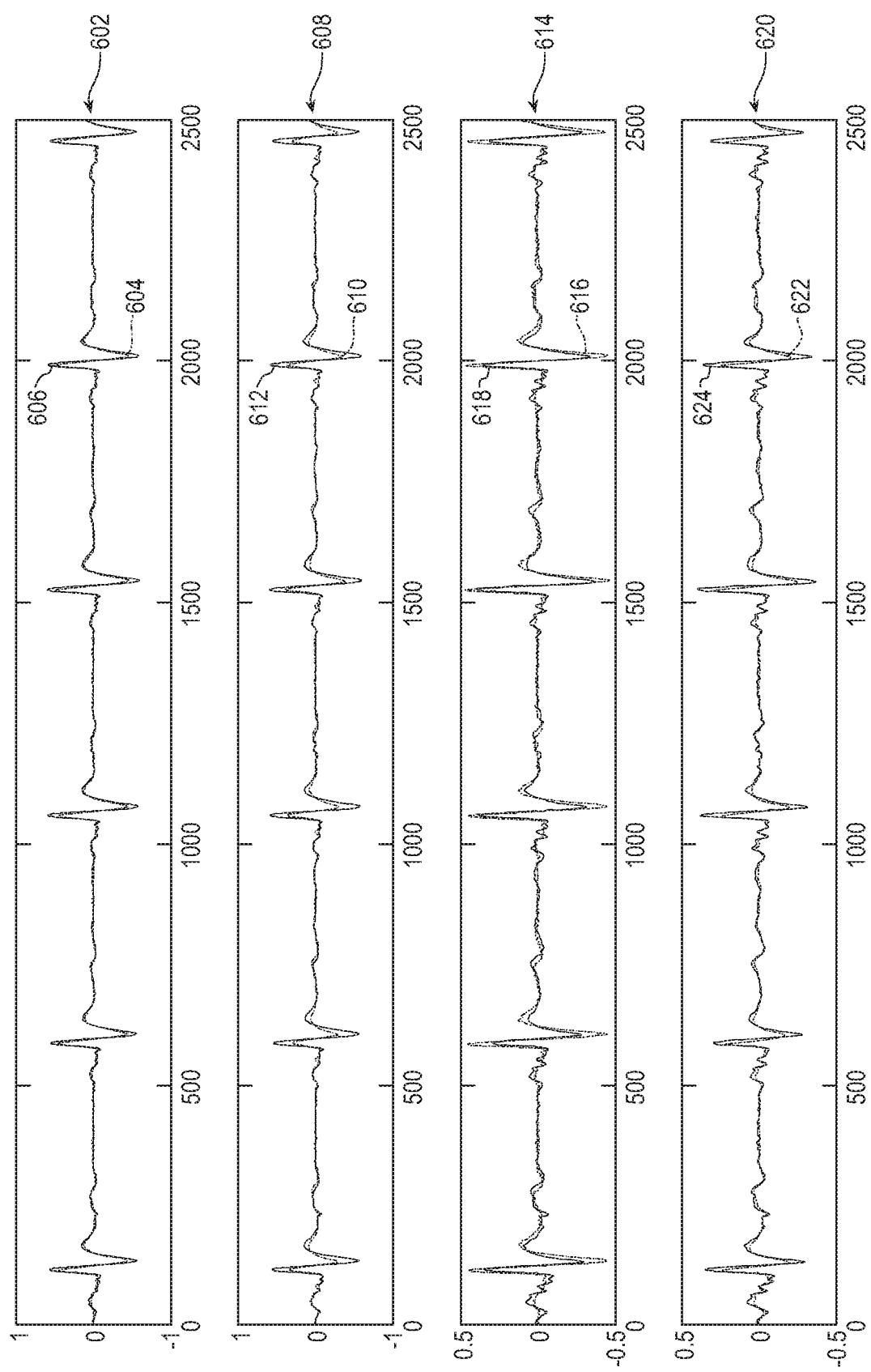
FIG. 6 illustrates differential vectors for normal sinus rhythm in accordance with exemplary embodiments described herein.
Figure 7:
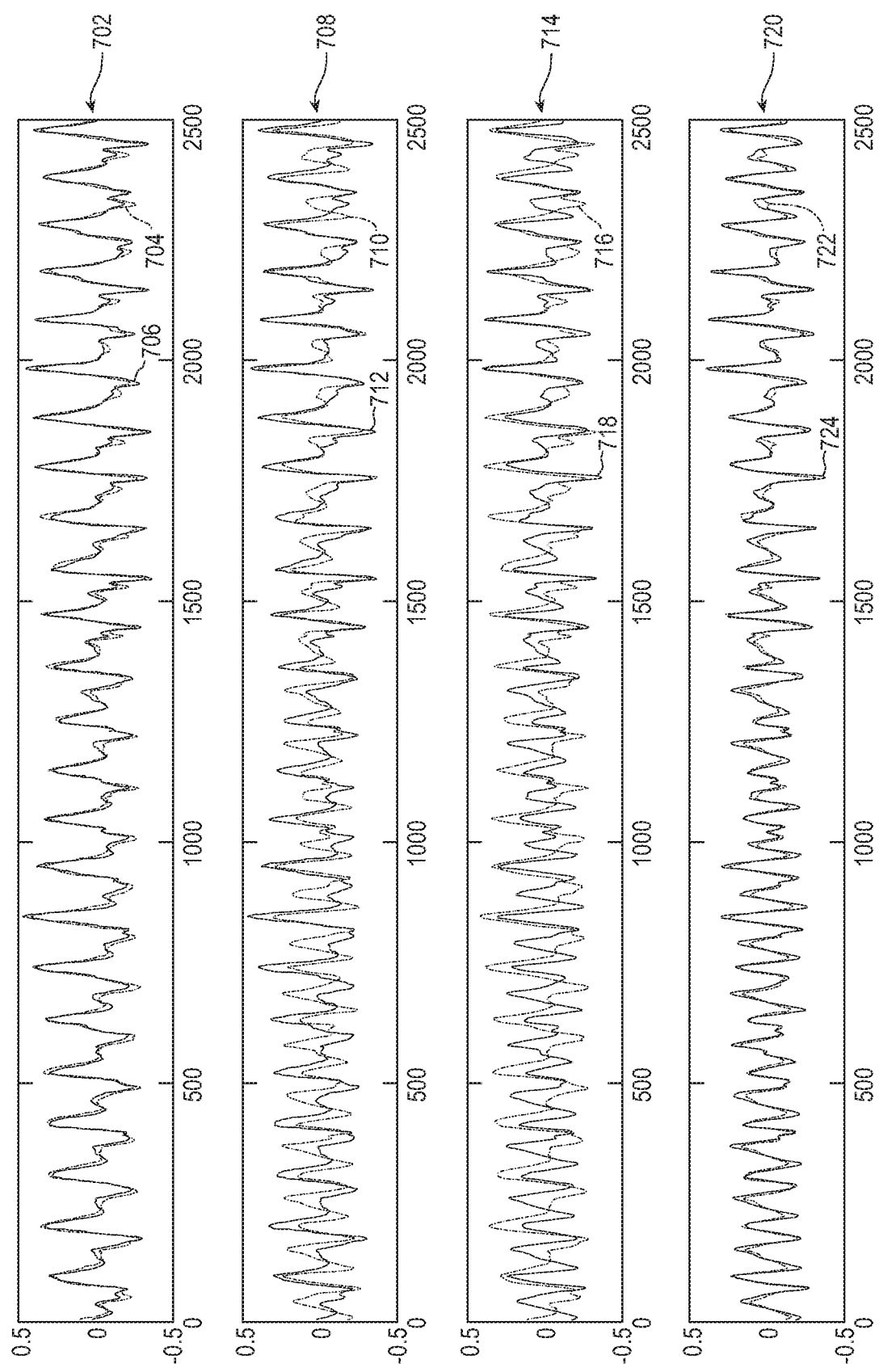
FIG. 7 illustrates for differential vectors for ventricular fibrillation in accordance with exemplary embodiments described herein.

FIGS. 6 and 7 illustrate examples of four different vectors listed in Table 1. FIG. 6 illustrates four differential vectors for NSR corresponding to the first row in Table 1. FIG. 7 illustrates four differential vectors for VF also corresponding to the first row in Table 1.

As can be seen in FIG. 6, the first row 602 compares the NSR readings for channel D 604 to channel C 606. The waveforms appear very similar therefore the correlation should be close to 1. The actual correlation is approximately 0.98. The second row 608 compares channel B 610 to channel D 612. Again, the waveforms are very similar, and the correlation is close to 1. The actual correlation is approximately 0.94. The third row 614 compares channel C 616 to channel F 618. The waveforms begin to deviate as compared to rows 602 and 608, but not significantly. The actual correlation of this row 614 is approximately 0.89. Finally, the fourth row 620 compares channel D 622 with the channel F 624. Again, the waveforms deviate slightly but the approximate FCC value is 0.91.

Referring now to FIG. 7, the first row 702 compares the VF readings for channel D 704 to channel C 706. The waveforms appear very similar therefore the correlation should be close to 1. The actual correlation is approximately 0.93. The second row 708 compares channel B 710 to channel D 712. Again, the waveforms are deviate, and the correlation is correlation is approximately 0.42. The third row 714 compares channel C 716 to channel F 718. The waveforms further deviate as compared to rows 702 and 708. The actual correlation of this row 714 is approximately 0.21. Finally, the fourth row 720 compares channel D 722 with the channel F 724. The waveforms come together again and correlate to 0.92.

As illustrated in Table 1 and in FIGS. 6 &7, the FCC values for channel F-channel C vary when comparing NSR and VF. During NSR, the propagation is more organized and consistent. During VF, the activity of the heart is more random and FCC value can be lower. During NSR, the potential difference E2 and E3 can be small. In contrast, in VF, the action potential may propagate from E2 to F3 and the potential difference can be larger. Therefore, the threshold for noise detection in NSR should be lower than FCC from VF otherwise VF would be determined to be noise. The potential difference between E1 and E4 is typically small, the correlation between channel D and channel C is higher than channel D and channel F for both NSR and VF. Therefore, in some embodiments, the threshold for noise detection of each comparison can be set individually rather than a single universal threshold. For example, the threshold can be set to 0.4 for channel D and channel C comparison and 0.1 for channel D and channel F.

Figure 8:
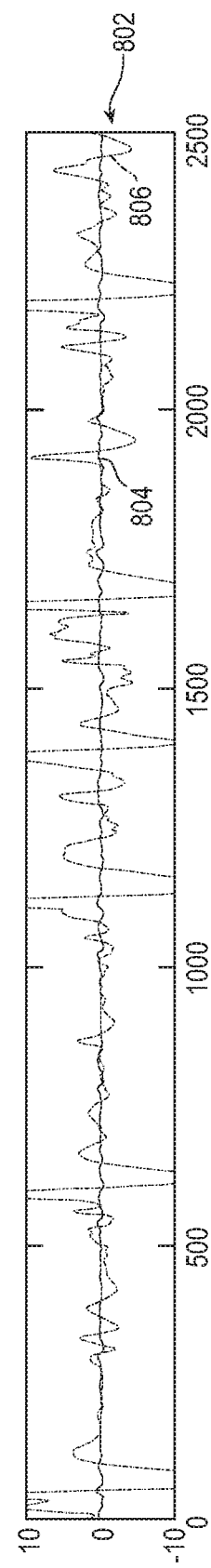
FIG. 8 illustrates non-correlated waveforms in accordance with exemplary embodiments described herein.

Referring to FIG. 8, if the correlation is too low from the expected value, then the correlation module 506 considers the situation noisy and suspends the rhythm analysis. For example, if electrode E3 is off and channels D 804 and C 806 show a poor correlation (e.g., FCC is equal to or less than 0.2), the correlation module 506 may conclude the noise level is too high to analyze the rhythm because, as described previously, channel D and channel C are expected to have a high FCC when F3 is off. In some embodiments, when the WCD detects an electrode is off, the channels including the off-electrode are exclude from the rhythm analysis. The correlation module 506 may then use the remaining channels for the analysis.

Referring back to FIG. 5, in some embodiments, the correlation module 506 measures the FCC value between channels using a segment with a fixed duration. For example, the correlation module 506 may use a fixed duration between 3 seconds and 15 seconds. In some embodiments, the fixed duration may be 5 seconds. In further embodiments, the correlation module 506 may measure the FCC value of each detected QRS complex. The correlation module 506 may then determine the noise level using the average value, the median value, the percentage, or some combination thereof of the well correlated beats. If the noise level is too high, then in some embodiments, the correlation module 506 may suspend the rhythm analysis. If the rhythm analysis is suspended for a predetermined period of time, in some embodiments, the correlation module 506 may send a signal to the alert module 504 which may generate an alert to the patient to address the issue.

Similarly, in some embodiments, the correlation module 506 may communicate with the action module 504 to send an alert to the patient when noise is detected in the system. In further embodiments, if no noise is detected by the correlation module 506 but a shockable rhythm is detected, the detection module 502 may communicate with the action module 504 to deliver an alert and a shock to the patient.

By calculating and comparing the FCC values, the correlation module 506 may not need to perform QRS detection or a separate noise level measurement such as peak amplitude or baseline shift. Furthermore, in some embodiments, the correlation module 506, using the FCC method described herein, may correctly categorize a rhythm analysis when a subtle noise is injected.

Figure 9:
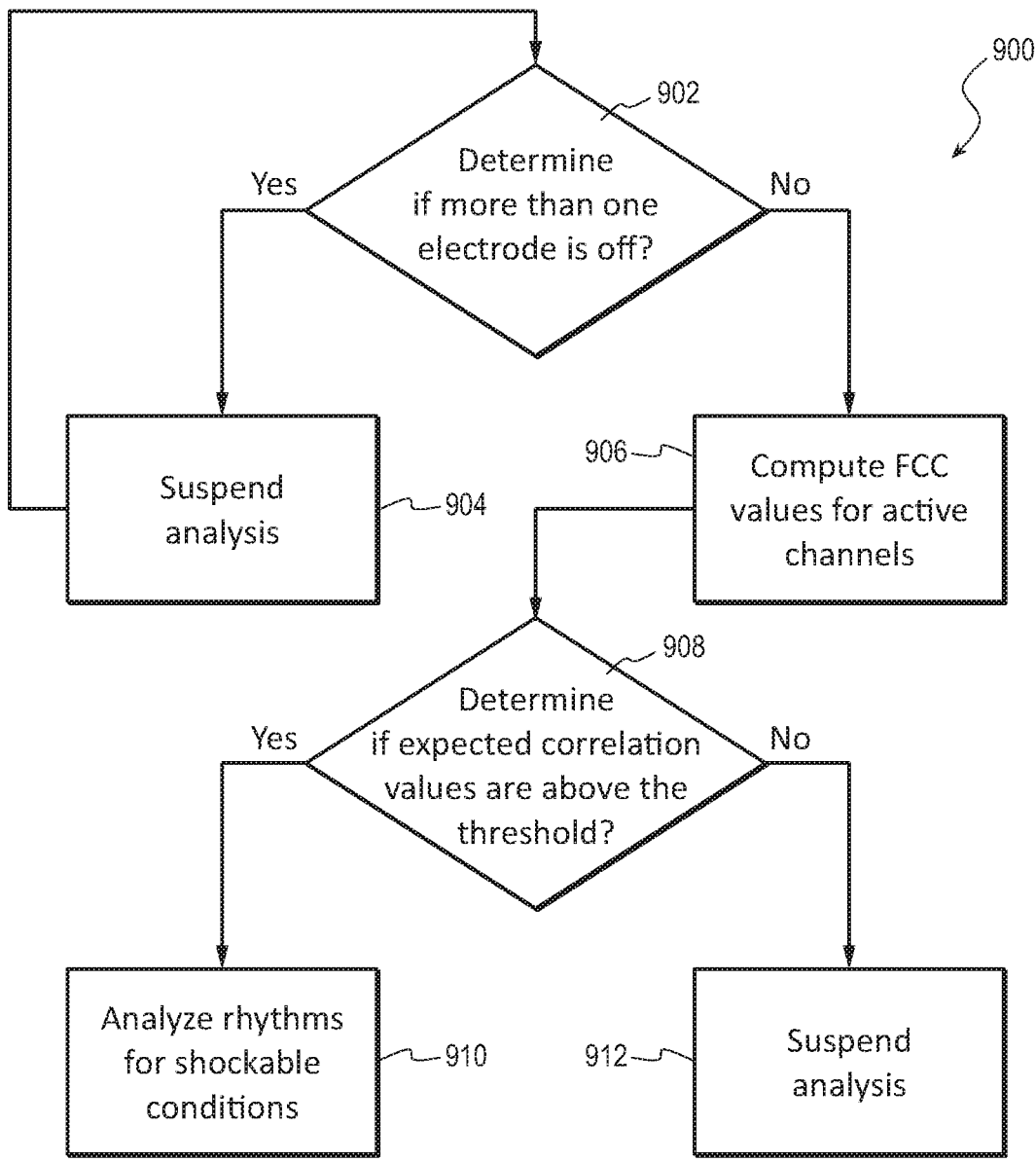
FIG. 9 is an exemplary flow diagram in accordance with exemplary embodiments described herein.

FIG. 9 is a flow chart illustrating an example of a method 900 for WCD systems, in accordance with various aspects of the present disclosure. For clarity, the method 900 is described below with reference to aspects of one or more of the systems described herein.

At block 902, the method 900 may determine if more than one electrode is off. If more than one electrode is off, then at block 904, the method 900 may suspend any analysis for a predetermined period of time. The analysis may be suspended for a few seconds or a few minutes depending on the patient and other circumstances. After the predetermined time period has elapsed, the method 900 may start over at block 902. If the method 900 has looped through this cycle for a predetermined number of times, the method 900 may alert the patient of a potential issue.

If only one or no electrodes are off, at block 906, the method 900 may compute the FCC values for the active channels. The method 900 may then determine, at block 908, if the expected correlations between channels are above a predetermined threshold. The predetermined threshold may be a single threshold used for all channels or may be a different threshold for each channel. If a single threshold is used for all channels, the predetermined threshold may be equal to or above 0.2. If a varying threshold is used, the predetermined threshold may be set between 0.1 and 0.4 for each channel. If the correlations are above the threshold, then at block 910, the method 900 may analyze the available rhythms for shockable conditions. If the correlations are below an analysis threshold, then at block 912, the method 900 may suspend the analysis. In some embodiments, the method 900 may suspend the analysis for a predetermined time period and then rerun the method 900. In other embodiments, if the expected correlations are not above a threshold, the method 900 may suspend the analysis and alert a patient of a potential issue with the system. In still further embodiments, the method 900 may rerun the analysis a predetermined number of times before alerting the patient of a potential electrode reading issue.

Thus, the method 900 may provide for detecting noise in an ECG signal. It should be noted that the method 900 is just one implementation and that the operations of the method 900 may be rearranged or otherwise modified such that other implementations are possible.

Figure 10:
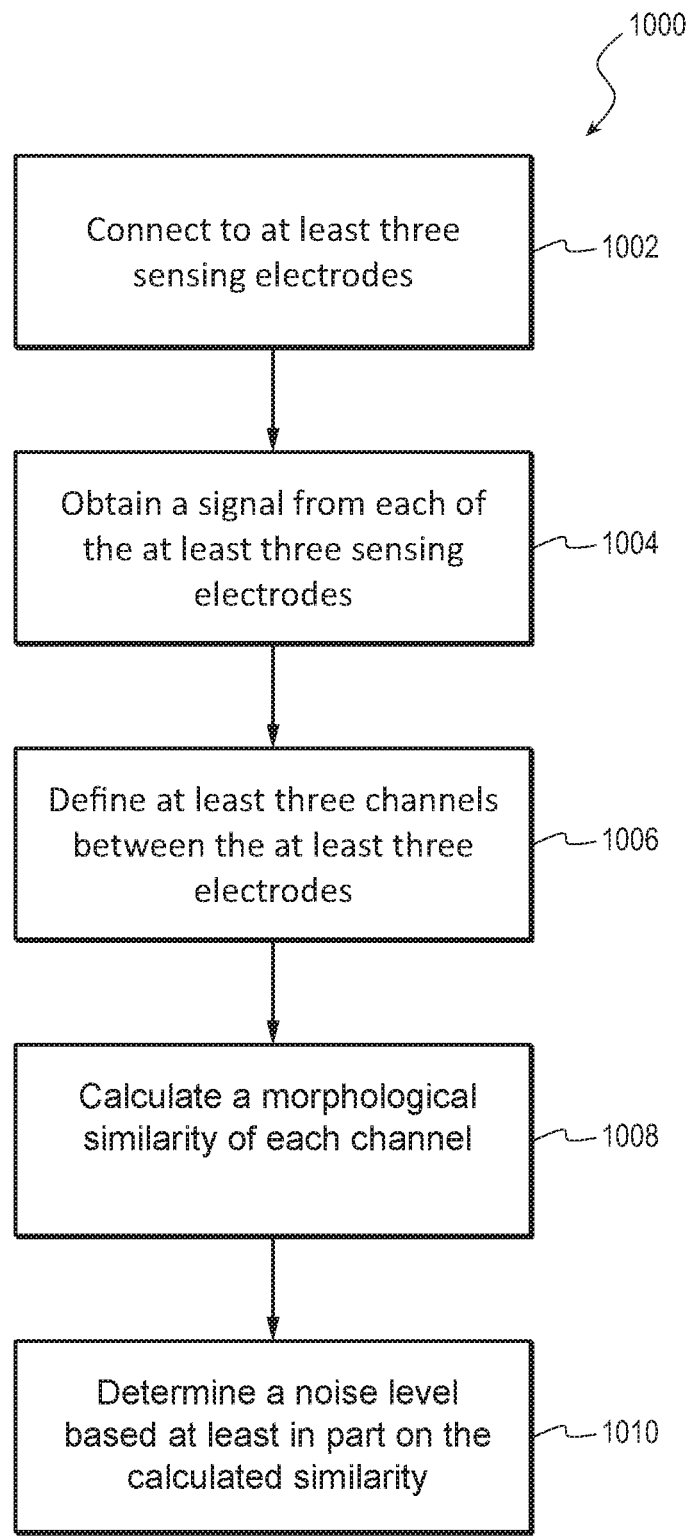
FIG. 10 is another exemplary flow diagram in accordance with exemplary embodiments described herein.

FIG. 10 is a flow chart illustrating an example of a method 1000 for WCD systems, in accordance with various aspects of the present disclosure. For clarity, the method 1000 is described below with reference to aspects of one or more of the systems described herein.

At block 1002, the method 1000 may connect to at least three sensing electrodes. For example, a system may have more than three electrodes, but one or more electrodes may be disconnected or otherwise have trouble connecting. At block 1004, the method 1000 may obtain a signal from each of the at least three sensing electrodes. The signal may be an ECG signal which the system may use to determine a health of a heart of a patient. At block 1006, the method 1000 may define at least three channels between the at least three sensing electrodes. For example, three vectors may be defined between sets of the at least three sensing electrodes. For example, if $E_1$, $E_2$, and $E_3$ are connected, the vectors comprise $E_1$-$E_2$, $E_1$-$E_3$, and $E_2$-$E_3$. Each vector may establish a channel. Once the channels are defined, at block 1008, the method 1000 may calculate a morphological similarity of each channel. In some embodiments, the morphological similarity may include an FCC value of each channel.

From the FCC value, at block 1010, the method 1000 may determine a noise level in the system based at least in part on the calculated morphological similarity. This may include comparing the FCC value. For example, if the calculated similarity is equal to or above a predetermined threshold, the method 1000 may determine that the signal is clean enough to analyze for a shockable rhythm. If the calculated FCC value is below a predetermined threshold, such as an analysis threshold, then the method 1000 may determine that the signal is too noisy to run a reliable analysis for a shockable rhythm. The method 1000 may then rerun the analysis and recalculate the morphological similarity. If the similarity value is again below the threshold, the method 1000 may issue an alert to the patient.

Thus, the method 1000 may provide for detecting noise in an ECG signal. It should be noted that the method 1000 is just one implementation and that the operations of the method 1000 may be rearranged or otherwise modified such that other implementations are possible.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A method to detect noise levels in electrocardiogram (ECG) signals for a patient, the method comprising:
   connecting to at least three sensing electrodes that includes a first sensing electrode located at a first location on the patient, a second sensing electrode located on a second location of the patient and a third sensing electrode located on a third location of the patient, the at least three sensing electrodes configured to monitor electrical activity of a heart of the patient;
   obtaining, during the monitoring by a cardiac monitoring device, a first signal from the first sensing electrode, wherein the first signal is based on a cardiac rhythm measured by the first sensing electrode at the first location during a first time period;
   obtaining, during the monitoring by the cardiac monitoring device, a second signal from the second sensing electrode, wherein the second signal is based on the cardiac rhythm measured by the second sensing electrode at the second location during the first time period;
   obtaining, during the monitoring by the cardiac monitoring device, a third signal from the third sensing electrode, wherein the third signal is based on the cardiac rhythm measured by the third sensing electrode at the third location during the first time period;
   defining, during the monitoring by the cardiac monitoring device, at least three channels between the at least three sensing electrodes;
   calculating, during the monitoring by the cardiac monitoring device, a morphological similarity value of at least one combination of the at least three channels by comparing the first signal with at least one of the second signal or the third signal; and
   determining, during the monitoring by the cardiac monitoring device, a noise level based at least in part on the morphological similarity value calculated, wherein the noise level is used at least in part in determining whether the patient has experienced an event of arrhythmia.

2. The method of claim 1, further comprising:
   establishing correlating channels based at least in part on the at least three channels, wherein the correlating channels have a similar morphological similarity value when no noise is present in the ECG signals; and
   calculating a morphological similarity value of each of the correlating channels.

3. The method of claim 2, further comprising:
   determining when the morphological similarity value of each of the correlating channels meets or exceeds a predetermined threshold.

4. The method of claim 2, further comprising:
   determining when the morphological similarity value of each of the correlating channels meets or exceeds a predetermined threshold.

5. The method of claim 3, further comprising:
   analyzing at least one of the first signal, the second signal or the third signal for a shockable heart rhythm when the morphological similarity value is above the predetermined threshold.

6. The method of claim 1, wherein calculating the morphological similarity value includes calculating feature correlation coefficient (FCC) values.

7. The method of claim 6, further comprising: suspending an ECG shockable analysis of the first signal, the second signal and the third signal when the FCC values are below a predetermined analysis threshold.

8. The method of claim 7, further comprising:
   obtaining an additional signal from each of the at least three sensing electrodes after the first time period has elapsed;
   calculating a second morphological similarity value of at least one combination of the at least three channels based at least in part on the additional signal obtained from each of the at least three sensing electrodes.

9. The method of claim 8, further comprising:
   issuing a noise alert to a person when the second morphological similarity value does not meet or exceed a predetermined threshold.

10. The method of claim 1, wherein the first time period is a fixed duration of between 3 and 15 seconds.

11. The method of claim 10, wherein the fixed duration is 5 seconds.

12. A method to detect noise levels in electrocardiogram (ECG) signals for a person, the method comprising:
    positioning at least four ECG sensing electrodes, the at least four ECG sensing electrodes configured to monitor electrical activity of a heart of the person at different locations on the person, wherein the at least four ECG sensing electrodes includes a first sensing electrode, a second sensing electrode and a third sensing electrode;
    obtaining, during the monitoring by a cardiac monitoring device, a first signal from the first sensing electrode, wherein the first signal is based on a cardiac rhythm measured by the first sensing electrode during a first time period;
    obtaining, during the monitoring by the cardiac monitoring device, a second signal from the second sensing electrode, wherein the second signal is based on the cardiac rhythm measured by the second sensing electrode during the first time period;
    obtaining, during the monitoring by the cardiac monitoring device, a third signal from the third sensing electrode, wherein the third signal is based on the cardiac rhythm measured by the third sensing electrode during the first time period;
    defining, during the monitoring by the cardiac monitoring device, at least three channels between the first sensing electrode, the second sensing electrode and the third sensing electrode;
    calculating, during the monitoring by the cardiac monitoring device, a morphological similarity value of at least one combination of the at least three channels based at least in part on comparing the first signal with at least one of the second signal or the third signal; and
    determining, during the monitoring by the cardiac monitoring device, a noise level based at least in part on the calculated morphological similarity value wherein the noise level is used at least in part in determining whether the patient has experienced an event of arrhythmia.

13. The method of claim 1, wherein calculating the morphology similarity value comprises calculating an ECG signal morphology, the ECG signal morphology being a shape of QRS complex waveforms.

14. The method of claim 1, further comprising:
    establishing, at a wearable cardioverter defibrillator (WCD), correlating channels based at least in part on the at least three channels, wherein the correlating channels have a similar morphological similarity value when no noise is present in the first signal, the second signal and the third signal; and
    calculating, at the WCD, a morphological similarity value of each of the correlating channels.

15. The method of claim 14, further comprising:
    determining, at the WCD, when the morphological similarity value of each of the correlating channels meets or exceeds a predetermined threshold.

16. The method of claim 15, wherein the predetermined threshold is equal to or above 0.2 at the WCD.

17. The method of claim 15, further comprising:
    analyzing, at the WCD, at least one of the first signal, the second signal or the third signal when the morphological similarity value is above the predetermined threshold.

18. The method of claim 15, wherein:
    calculating the morphological similarity value includes calculating feature correlation coefficient (FCC) values, and
    the method further comprises suspending, at the WCD, an ECG shockable analysis of the first signal, the second signal and the third signal when the FCC value is below a predetermined analysis threshold.

19. The method of claim 12, further comprising:
    establishing, at a wearable cardioverter defibrillator (WCD), correlating channels based at least in part on the at least four ECG sensing electrodes, wherein the correlating channels have a similar morphological similarity value when no noise is present in the ECG signals; and
    calculating, at the WCD, a morphological similarity value of each of the correlating channels.

20. The method of claim 19, further comprising:
    determining, at the WCD, when the morphological similarity value of each of the correlating channels meets or exceeds a predetermined threshold.

* * * * *